(12) United States Patent
Karim et al.

(10) Patent No.: US 11,147,529 B2
(45) Date of Patent: Oct. 19, 2021

(54) METHOD AND APPARATUS FOR SPECTRAL ADJUSTMENT IN DIGITAL X-RAY IMAGING

(71) Applicant: KA IMAGING INC., Waterloo (CA)

(72) Inventors: Karim S. Karim, Waterloo (CA); Sebastian Lopez Maurino, Kitchener (CA)

(*) Notice: Subject to any disclaimer, the term of this patent is extended or adjusted under 35 U.S.C. 154(b) by 0 days.

(21) Appl. No.: 17/105,579

(22) Filed: Nov. 26, 2020

(65) Prior Publication Data

US 2021/0153835 A1   May 27, 2021

Related U.S. Application Data

(60) Provisional application No. 62/941,048, filed on Nov. 27, 2019.

(51) Int. Cl.
*A61B 6/00* (2006.01)

(52) U.S. Cl.
CPC .............. *A61B 6/58* (2013.01); *A61B 6/4035* (2013.01); *A61B 6/4208* (2013.01); *A61B 6/461* (2013.01)

(58) Field of Classification Search
CPC ....... A61B 6/58; A61B 6/4035; A61B 6/4208; A61B 6/461
See application file for complete search history.

(56) References Cited

U.S. PATENT DOCUMENTS

| 2005/0163283 A1 | 7/2005 | Bruder et al. |
| 2012/0301002 A1* | 11/2012 | Flohr .................. A61B 6/5235 382/131 |
| 2014/0029819 A1 | 1/2014 | Zeng et al. |
| 2017/0238887 A1* | 8/2017 | Karim ................... G01T 1/2018 |
| 2019/0159741 A1 | 5/2019 | Fredenberg et al. |
| 2019/0290227 A1* | 9/2019 | Krauss ................ G06T 11/006 |

OTHER PUBLICATIONS

Canadian Intellectual Property Office as International Searching Authority, Search Report for International Application No. PCT/CA2020/051619, dated Feb. 16, 2021.
Canadian Intellectual Property Office as International Searching Authority, Written Opinion for International Application No. PCT/CA2020/051619, dated Feb. 16, 2021.

* cited by examiner

*Primary Examiner* — Dani Fox
(74) *Attorney, Agent, or Firm* — Gowling WLG (Canada) LLP; Jeffrey W. Wong

(57) ABSTRACT

A method and system for spectral adjustment for a digital X-ray imaging system. The method includes obtaining a set of initial digital X-ray images and then weight factoring the images to generate a set of weight factored digital X-ray images. The weight-factored digital X-ray images are then combined to generate a composite image that is spectrally distinct from the set of initial digital X-ray images.

20 Claims, 4 Drawing Sheets

METHOD AND APPARATUS FOR SPECTRAL ADJUSTMENT IN DIGITAL X-RAY IMAGING

CROSS-REFERENCE TO OTHER APPLICATIONS

The current disclosure claims priority from U.S. Provisional Application No. 62/941,048 filed Nov. 27, 2019, which is hereby incorporated by reference.

FIELD

The disclosure is generally directed at X-ray imaging, and more specifically, at a method and apparatus for spectral adjustment in digital X-ray imaging.

BACKGROUND

Radiological examinations are seen as examinations that use X-ray imaging technology such as, but not limited to, digital radiography, computer tomography, fluoroscopy or related techniques to generate digital images to assist users to visualize body spaces and organs and their functions. The use of these types of examinations has resulted in an improvement in helping medical professionals prepare a diagnosis for a patient. While widely used, there are some disadvantages with these examination systems.

Image retake of radiological examinations not only increases the risk of radiation exposure to a patient and/or medical professional, but also wastes medical resources and degrades the quality of service. Some of the causes of image retakes are typically mispositioning, bad technique and general artifacts, patient movement, data processing and transfer errors. Various academic publications have reported image retake rates for chest and abdominal X-rays to be between 5% and 15% respectively with over/under exposure accounting for up to 20-30% of total retakes. Although retakes due to mispositioning, artifacts and inadequate inspiration can be addressed by proper training, retakes due to over/under exposure persist due to the complex nature of predicting the ideal exposure setting for each patient. This continues to be true even with the advent of wider dynamic range digital radiography (DR) X-ray imaging equipment. Today, when more than 2 billion annual X-ray exams are undertaken globally, retakes due to over and under exposure range continue to represent a valid concern in diagnostic imaging. Moreover, in other X-ray imaging applications (e.g. dynamic imaging), determining the optimal X-ray energy for visualization can also require retakes and repeated imaging of the same region of interest.

Thus, there is provided a method and apparatus for spectral adjustment in digital X-ray imaging that overcomes disadvantages of current systems.

SUMMARY

The disclosure is directed at a method and apparatus for spectral adjustment in digital X-ray imaging. In one embodiment, the disclosure includes obtaining a set of at least two initial images including distinct spectral information, weight factoring the at least two initial images and then combining the weight factored images to generate a composite image that includes spectral information that is distinct from the set of two initial images.

In one aspect of the disclosure, there is provided a method of digital spectral adjustment for digital X-ray imaging including obtaining at least two images generated by an X-ray imaging system, each of the at least two images including spectral information, the spectral information of each of the at least two images being distinct from each other; applying a weighting factor to the at least two images to generate weight factored images for each of the at least two images; and generating a composite image by combining the weight factored images of the at least two images wherein the composite image is spectrally distinct from the at least two images.

In another aspect, generating a composite image includes performing a linear combination of the weight factored images of the at least two images. In a further aspect, generating a composite image includes performing a non-linear combination on the weight factored images of the at least two images. In yet another aspect, applying a weighting factor includes applying a same weighting factor to each of the at least two images. In an aspect, applying a weighting factor includes applying a different weighting factor to each of the at least two images. In a further aspect, applying a weighting factor includes applying a predetermined weighting factor to each of the at least two images. In another aspect, applying a weighting factor includes receiving an input from a user; and determining the weighting factor based on the input from the user. In yet another aspect, before applying a weighting factor: receiving the weighting factor from a user. In yet a further aspect, the method includes calculating X-ray source settings based on characteristics of the composite image; and displaying the calculated X-ray source settings. In another aspect, the calculated X-ray source settings include a kVp setting or a filtration setting.

In another aspect, the method is used in dynamic interventional medical imaging applications and the weighting factor is a value less than 1. In a further aspect, the method is used in digital X-ray imaging of a multi-material object. In yet another aspect applying a weighting factor includes applying different weighting factors to each of the at least two images based on an area of interest of the multi-material object. In yet another aspect, the method is used in radiotherapy or radiosurgery. In a further aspect, generating a spectrally distinct composite image includes generating a spectrally distinct composite image at lower kVp settings.

In another aspect of the disclosure, there is provided a computer-implemented method for spectral adjustment for digital X-ray imaging including under the control of one or more computer systems configured with executable instructions, obtaining at least two images generated by an X-ray imaging system, each of the at least two images including spectral information, the spectral information of each of the at least two images being distinct from each other; applying a weighting factor to the at least two images to generate weight factored images for each of the at least two images; and generating a composite image by combining the weight factored images of the at least two images wherein the composite image is spectrally distinct from the at least two images.

In another aspect, the generating a composite image includes performing a linear combination of the weight factored images of the at least two images. In a further aspect, generating a composite image includes performing a non-linear combination on the weight factored images of the at least two images.

In a further aspect of the disclosure, there is provided an X-ray imaging system including an X-ray source; a multi-layer X-ray detector for generating a set of at least two initial images; and a processor for weight factoring the at least two initial images to generate a weight factored image for each of the set of at least two initial images and for combining the weight factored images to generate a composite image, wherein the composite image is spectrally distinct from each of the at least two initial images.

In another aspect, the processor is integrated within the multi-layer X-ray detector.

DESCRIPTION OF THE DRAWINGS

Embodiments of the present disclosure will now be described, by way of example only, with reference to the attached Figures.

DESCRIPTION

Figure 1:
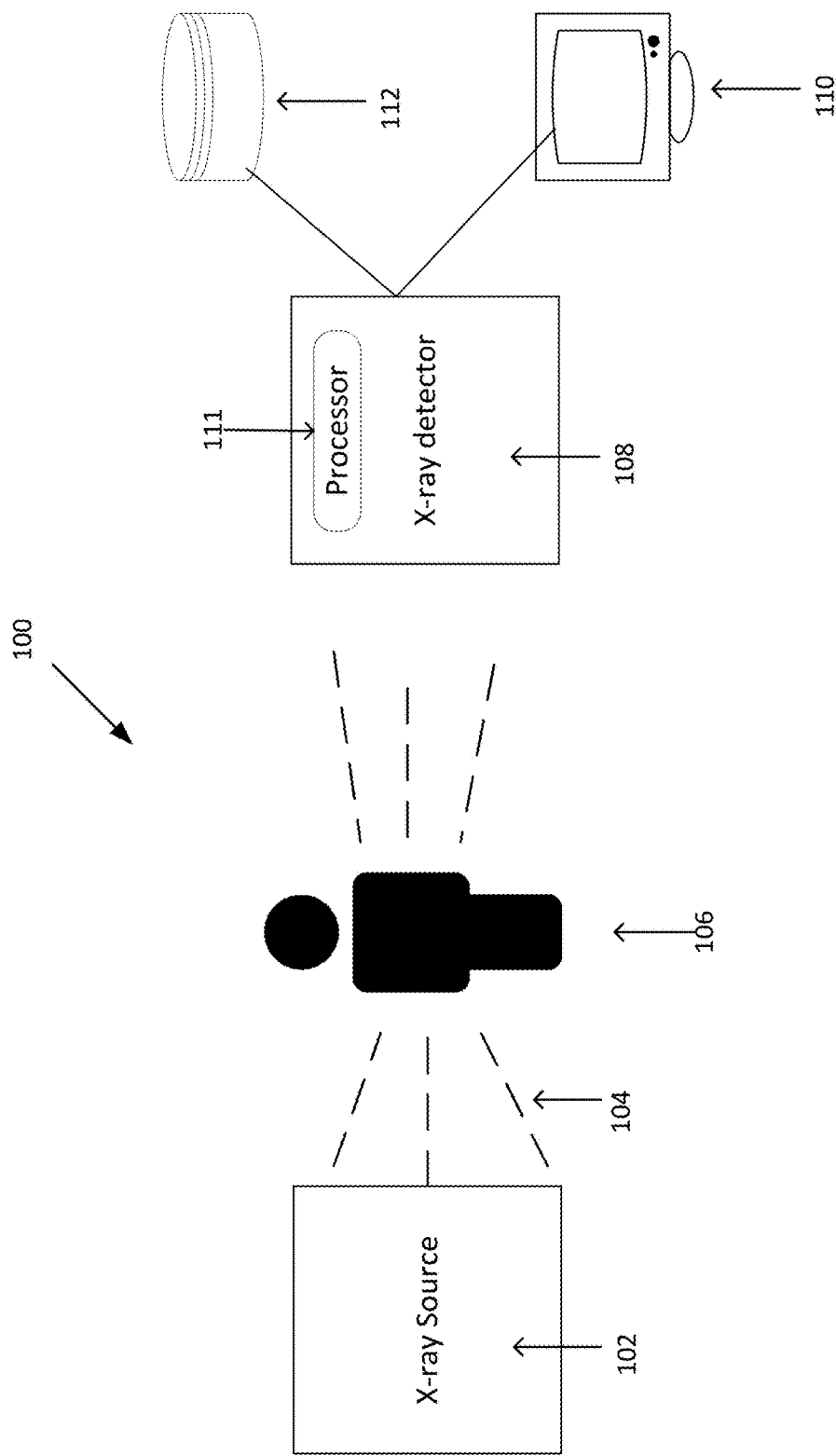
FIG. 1 is schematic diagram of a digital X-ray imaging system.
Figure 2:
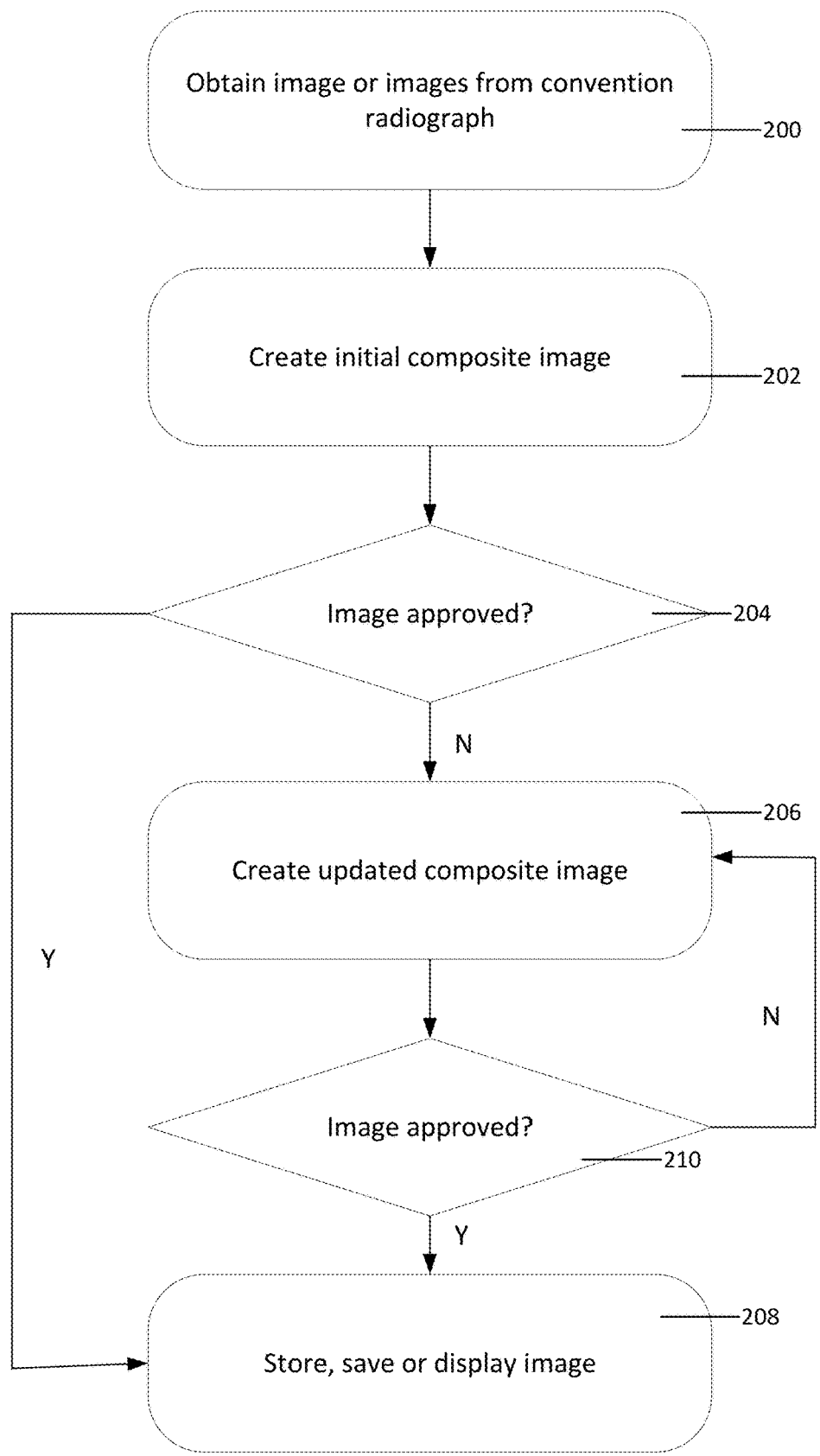
FIG. 2 is a flowchart of a method of spectral adjustment for a digital X-ray imaging system.

The disclosure is directed at a method and apparatus for spectral adjustment in digital X-ray imaging. In one embodiment, the disclosure includes obtaining a set of at least two initial images including distinct spectral information, weight factoring the at least two initial images and then combining the weight factored images to generate a composite image that includes spectral information that is distinct from the set of two initial images. One advantage of the current disclosure is that a patient and/or medical professional, such as a clinician, may experience less exposure to radiation compared to current systems.

In digital radiography (DR) systems, X-ray images of a patient are taken which expose the patient, and, possibly, a medical professional assigned to take the X-ray images to radiation. In some cases, retakes are necessary, thereby exposing the patient and the medical professional to at least another dose of radiation. These retakes may be required, for instance, if an incorrect exposure is experienced. An incorrect exposure is caused by selection of exposure parameters such as, but not limited to, X-ray source peak kilovoltage (kVp) and exposure current-time multiples (mAs) that result in an image that does not meet predetermined requirements. For example, selecting a kVp and/or mAs value that is lower or higher than an optimal or preferred value generally results in an incorrect exposure.

A, preferred, correct (or "optimal") kVp setting or value with mAs values that are lower or higher than an "optimal" value with respect to the kVp setting will yield a loss of image contrast because there are either too few or too many photons. However, this is often correctable in DR equipment by leveraging the wider dynamic range of digital X-ray equipment and post-processing with conventional linear windowing and offset. It should be noted, though, that a low mAs setting could still yield a grainy looking image even after corrections.

If an incorrect kVp setting or value is used, there is less flexibility in post-processing thereby generating an image that does not meet predetermined requirements. Non-optimal kVp images are typically not correctable using linear offset and windowing techniques, even with wider dynamic range DR devices because the overall and relative X-ray penetration across the image may not yield an ideal contrast. It is the increase in the ratio of high energy to low energy photons that results in poor image contrast when a high kVp setting is used to image a low density object (e.g. a thin patient). Poor image contrast resulting from non-optimal kVp settings is different from non-optimal mAs settings which simply refer to either too many or too few photons, where the ratio of high to low energy photons for different mAs values is preserved. Therefore, it is hard with conventional X-ray imaging systems to correct for this ratio inadequacy with post-processing techniques, and so a retake is often necessary thereby exposing the patient and/or the medical professional to more radiation. The current disclosure provides improvements over these current techniques.

In one method of the disclosure, to overcome or reduce the need for retakes, such as due to incorrect kVp settings, the method includes making use of energy data contained in the X-rays passing through the patient.

Turning to FIG. 1, a schematic diagram of an X-ray system in accordance with an embodiment of the disclosure is shown. As shown in FIG. 1, the system 100 includes an X-ray source 102 that directs source X-rays 104 towards a patient 106 and an X-ray detector 108 that senses, or receives, the transmitted X-rays 108 after they have passed through the patient 106, or specimen. The positioning of the X-ray source 102 and the X-ray detector 108 with respect to the specimen will be understood.

In an embodiment, the X-ray detector 108 is capable of resolving different X-ray energies bands of the X-ray spectrum incident on or that is sensed by the detector 108. In another embodiment, the X-ray detector 108 may include multiple stacked sensitive sensor, or detector, layers with optional filtering materials between them. This results in a higher proportion of high-energy photons reaching each detector layer, thereby enabling the detector to obtain multiple energy bands or at least two images with spectrally distinct information. In another embodiment, different energy bands, or different images with spectrally distinct information, may be obtained or sensed by the detector 108 through multiple exposures that utilize different kVp (and possibly different mAs) values. Since an increasing kVp value will result in an input X-ray spectrum of increasing proportion of high-energy X-rays, it may be possible to obtain measurements of energy bands of increasing energy by increasing kVp values.

In a further embodiment, energy information is obtained by the detector 108 through the use of single photon counting X-ray detectors with energy discrimination. In this embodiment, the energy of some absorbed X-ray photons may be classified in a set of pre-determined bands at the time of absorption, thereby splitting the input spectrum into two or more bands or two or more images with spectrally distinct information. More generally, X-ray detector and system technologies that are able to perform some X-ray spectrum analysis such as resolving individual photon energies or at the least, energy bands are contemplated where the resolution may result in at least two images with spectrally distinct information. In each embodiment of the disclosure, at least two energy bands, or images with spectrally distinct information, are obtained to enable improvement for non-optimal kVp settings.

When obtaining a final X-ray image with an energy-resolving X-ray system as described above, in one embodiment, the method of the disclosure includes the computation, formation or generation of one or more composite images, one at a time, until one of the composite images meets predetermined requirements. There requirements may be based on a medical professional's review or may be based on requirements that are pre-stored within the system such as within a processor 111 that may be part of the X-ray detector 108 (as shown in FIG. 1) or may be external to the X-ray detector 108 but in communication with the detector. The processor 111 may include computer executable instructions that, if executed, provide a method of spectral adjustment in a digital X-ray imaging system.

As each composite image is generated, it may be displayed to the operator of the system (such as the medical professional) such as via a display 110 or may be stored in a database 112 for access at a later time, for access by a remote user or may be displayed and stored. This composite image may be seen as a replacement for or improvement of a conventional radiograph.

Assuming an X-ray detector having a set of stacked sensors, a conventional radiograph will include multiple images obtained from each of the set of stacked sensors. The system and method of the disclosure then combines these images together as will be discussed below.

In order to generate or compute a composite image, this may be done by initially selecting or retrieving at least two images that are obtained by the detector (200). In one embodiment, multiple energy images are obtained as discussed above. As understood, these multiple energy images contain energy band information. Alternatively, each of the obtained images include spectral information that is distinct from the other obtained images.

The at least two images are then weighted, or weight factored, to assist in the creation or generation of an initial composite image (202), such as by combining the weight factored images with the initial composite image being spectrally distinct from each of the obtained images. In an alternative embodiment, the spectral information of each of the obtained images may be weight factored. As will be understood, images are typically generated based on numerical values associated with the image and, in one embodiment, it is these numerical values that are weight factored and then combined to generate a single composite image from the at least two images having spectrally distinct information. In a further embodiment, the weighting factor may be the same value for each of the different images or the weighting factor may be a different value, or not the same value, for each of the different images depending on the application for which the disclosure is being used. In another embodiment, the weighting factors may be based on default parameters.

A check is then performed to determine if the initial composite image is approved (204). This may be done by displaying the initial composite image to the medical professional for review (and the receiving a response from the medical professional) or may be done by the system which may process the composite image for predetermined requirements, such as, but not limited to, contrast to noise characteristics or frequency power spectral shape.

If the initial composite image is not approved, an updated composite image is generated (206). In order to generate the updated composite image, the weighting factors are updated or changed such that a new composite image is generated. The updated or new composite image will also be spectrally distinct from each of the obtained images. The weighting factors may be updated based on input from the medical professional or may be updated based on calculations or determinations by the system. These determinations may be based on pre-stored parameters or may be based on the weight factoring values for the initial composite image. If the initial composite image is approved, this image is stored, saved or displayed (208). The stored, saved or displayed image can then be seen as the final image.

The updated composite image is also checked to see if it is approved (210). If it is not, another updated composite image is generated (206), such as by further updating or changing the weighting factors. If the updated composite image is approved, this updated composite image is then stored, saved or displayed (208) and seen as the final image. Based on this final image, or any of the composite images, the system may calculate X-ray source settings that may have been used to produce the image. This calculation may be based on the characteristics of the composite image. These characteristics may also include the weighting factor or factors or may not include the weighting factor or factors. In one embodiment, the X-ray source settings may be seen as estimated X-ray source settings. These X-ray source settings may include a kVp setting, a filtration setting or both. Alternatively, the system may calculate an approximate kVp value that would be associated with the final image such that this information may be provided to the medical professional for possible use in future examinations.

Figure 4:
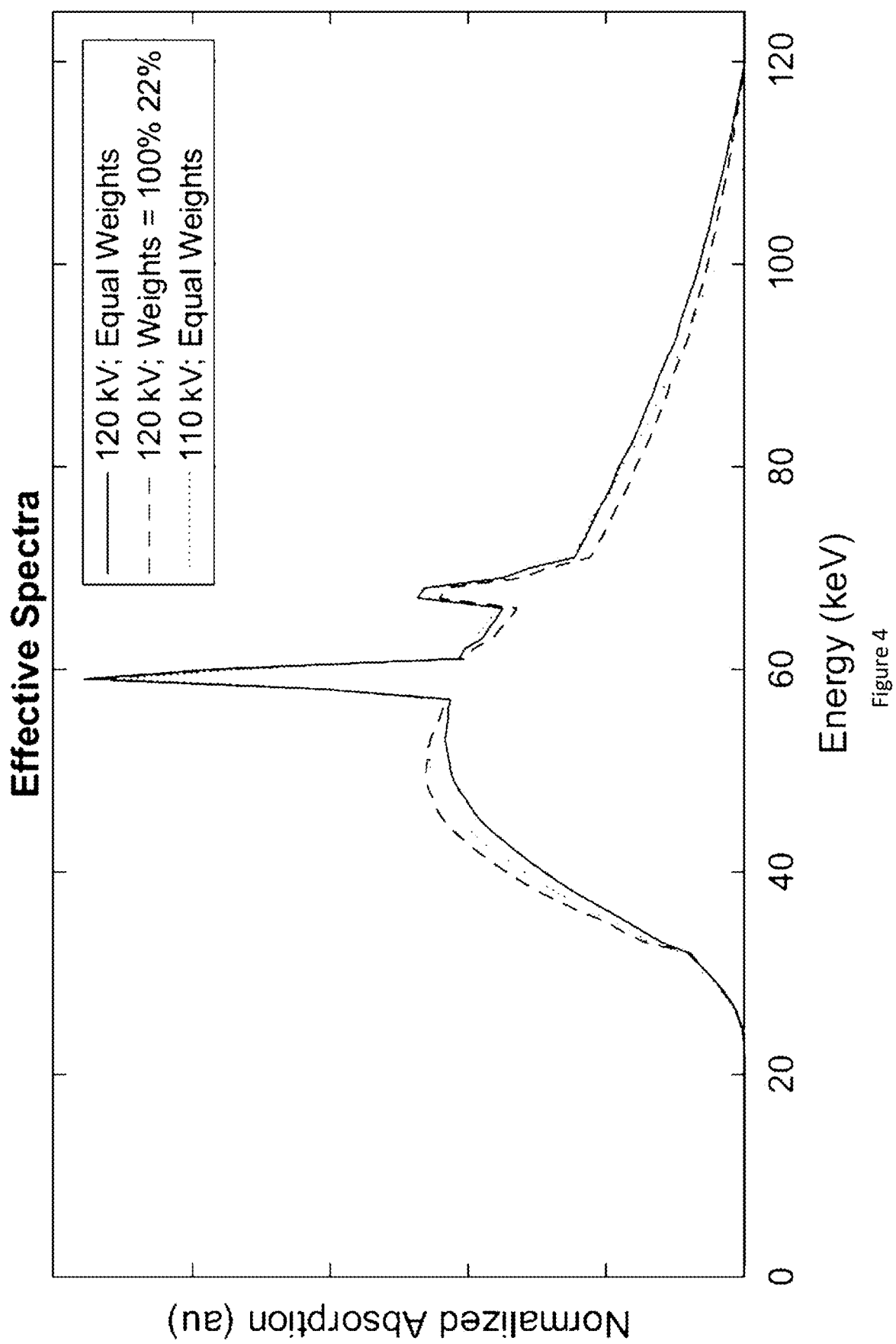
FIG. 4 is a graph showing X-ray spectra of the performed, ideal, and compensated images.

FIG. 4 illustrates a graph showing a comparison of the energy information associated with an image in a few different scenarios. Each of the scenarios show a simulated spectrum filtered by an approximation of a human chest and absorbed in a dual-layer X-ray detector. In the current graph, each layer contains an approximately 350 μm CsI layer as its X-ray sensitive material. In this example, the energy-discrimination capabilities of the X-ray system are achieved via the multi-sensor detector. Initially, two initial, or layer, images are detected by the dual-layer X-ray detector.

A first scenario shows an effective spectrum of an initial composite image that is generated by combining the two layer images after the two layer images have been weight factored with equal weighting factors. This set of weighting factors can be considered the default set for this example. The user may then select weightings factors of 100% and 22% for the top and bottom layer images respectively as a second configuration (or updated composite image) for the obtained images. The system may then be able to estimate— using certain assumptions about the source X-ray spectrum and average patient absorption—that an image acquired at 110 kV could have yielded similar image contrast properties to the updated, or second, composite image if the default weight factors had been used. FIG. 4 shows this new spectrum and how it closely resembles the effective spectrum of the second composite image. This information may then be provided to the user to advise the user to change their source kVp setting to 110 kV to achieve a desired contrast by default, or to change the default weighting factors to 100% and 22%.

In one embodiment, the system and method may be seen as taking at least two images having spectral distinct information and generating a single final image that is a combination of the at least two images where the at least two images have been weight factored.

The effective spectrum of the initial or any of the updated composite images follows from the equation and parameters utilized in its computation. A common way of generating the initial or any of the updated composite images is by a linear combination of all energy, or obtained, images:

$$I_c = \sum_i^n w_i I_i$$

where $I_c$ is the composite image, n is the number of energy images acquired, $I_i$ are each of the energy images and $w_i$ are the individual weights given to each layer. In the simplest form, all images are weighted equally, such that $w_i = w_1 \forall i$.

However, it is possible to apply different weighting factors to each of the retrieved images or energy images, thereby weighing each energy band, or spectrally distinct information, differently in any of the individual composite images. This allows for a post-acquisition modification of the energy spectrum used to generate the each of the individual composite images. It is also possible to combine the images in a non-linear manner, in which case more or different parameters may be used. For example, different spatial frequency bands may be weighted differently, by first splitting the obtained images by using a low-pass and high-pass filter, and then applying individual weighting factors to each of these sub images. It is the ability to modify these weighting factors, or parameters, post-acquisition that provides an aspect of novelty to the disclosure, regardless of the specific composite image equation.

By modifying the spectrum of either the initial or any of the composite images, the relative contributions of X-ray energies can be tuned, and hence it is possible to correct for some or all of the defects in a composite image that is deemed to be lacking in kVp-related contrast. In other words, with this method it is possible to compute a final image that simulates a different kVp setting (that what was originally used), thus allowing the operator (of the X-ray system) some flexibility to correct for image errors after the exposure, thereby removing or reducing the need for a retake. The user, or medical professional, may use the method of the disclosure to dynamically alter the X-ray bands proportions while evaluating the result in order to find or determine an improved overall image contrast.

Figure 3:
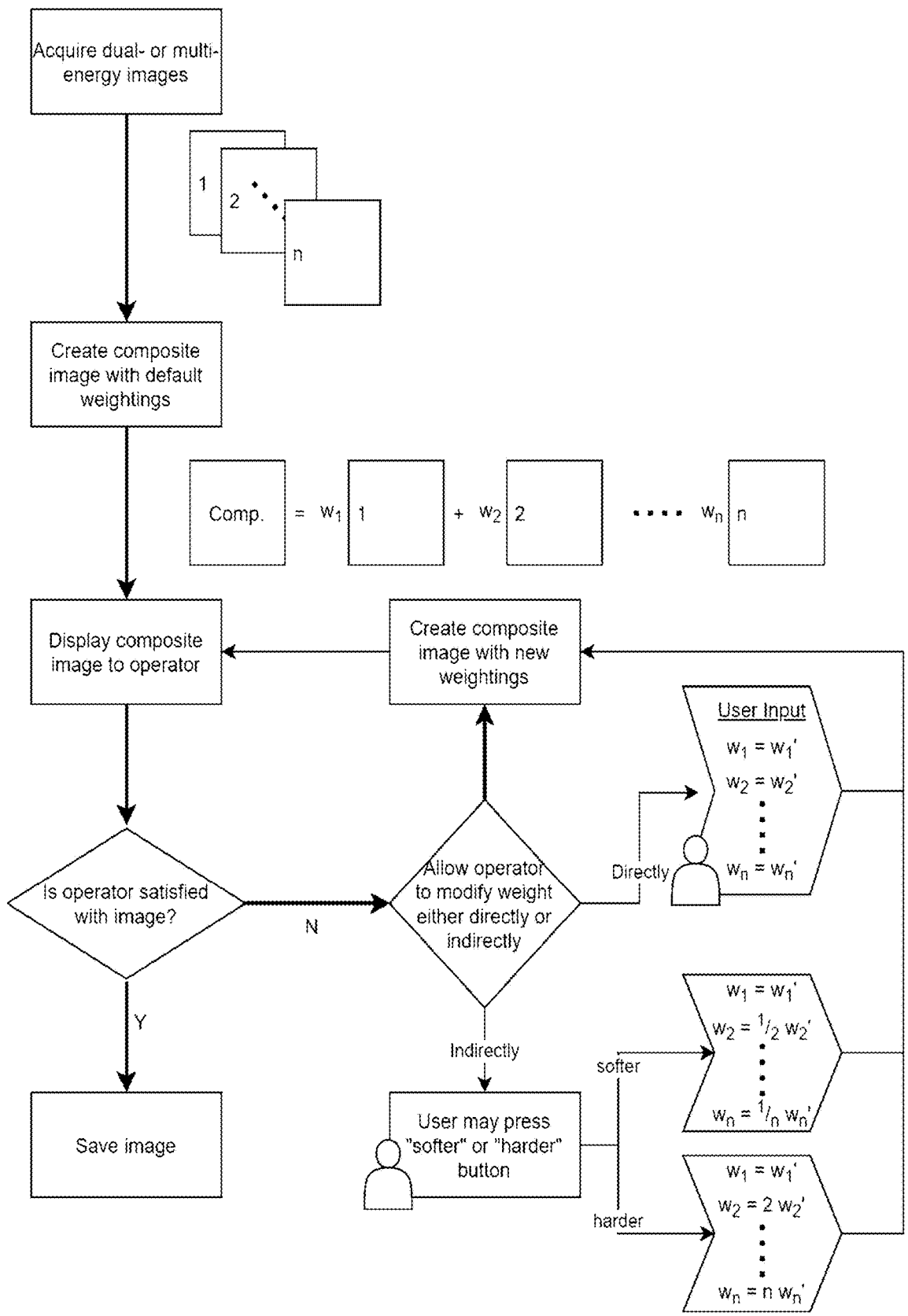
FIG. 3 is a flowchart of another method of spectral adjustment for a digital X-ray imaging system.

Turning to FIG. 3, another embodiment of a method of generating a composite image (or a final image) is shown. As shown in the flowchart of FIG. 3, the disclosure does not just allow for pre-computed compensations, but also allows a user (such as the medical professional) to dynamically modify any of the composite images after acquisition. Modifications may be done continuously until the user is satisfied with the obtained composite image. In some embodiments, the user may be asked to directly input the weighting factors that the user would like to be used to generate the composite image, or this process may be abstracted away from the user, where simpler interaction mechanisms are presented to the user and the weighting factors are computed in the background. These interaction mechanisms may include, but are not limited to, generating a harder or softer image whereby the user select one of the interaction mechanisms and weighting factors would automatically be selected, or calculated, by the system to generate an updated composite image obtained with a harder or softer input spectra, respectively.

Initially, at least two, or multiple, energy images are obtained through one of the embodiments as discussed above. Each of these images contain their own energy band information whereby the energy band information for one image may be seen as information that is spectrally distinct from the energy band information of any of the other images. In one embodiment, each image contains information from a higher average X-ray energy band. An initial composite image is then computed or generated using default parameters such as with a weighting factor of one (1) for each of the images. In this embodiment, the composite image is computed as a linear combination of all of the selected images with their weighting parameters $w_{1 \ldots n}$.

Next, this initial composite image is displayed to the user. At this point, the user may decide that they are satisfied with the quality of the initial composite image and hence save it. If, however, they determine that the image suffers from some kVp-related contrast deficiencies, the user may choose to re-compute it by using an updated set of parameters or weighting factors. An updated composite image may then be generated using the new parameters or weighting factors.

The weighting factors may be inputted directly or indirectly by the operator. In a direct input method, the user selects the weighting factors. In one embodiment, this is achieved through a user interface including a slide bar that allows the user to select the weighting factor for each obtained energy image. For example, in a dual-energy system, the user may select a weighting factor of 100% for a low-energy image and a weighting factor of 25% for a high-energy image. In an indirect input method, the determination or calculation of numerical values for the weighting factors may be abstracted away from the operator. In one embodiment, this may achieved by presenting a "softer" and "harder" button to the operator (such as via a user interface). Selection of the "softer" button updates the previously selected, or used, weighting factors and scales the weighting factors with a predetermined value. In one embodiment, the predetermined value may be reciprocal to image number, as it is understood that higher numbered images contain higher energy information, and a softer X-ray beam is one with lower average energy. Conversely, selection of the "harder" button may scale the weighting factors directly proportionally to their layer number. However, it is understood that this scaling method is only one embodiment of how the weighting factors may be determined or calculated by the system, and that many methods of numerical abstraction between user input and weighting factor modification are contemplated.

The user is then presented with the updated composite image computed with the new set of parameters, and may decide if they are satisfied with it or would like to continue re-computing another single composite image with further new parameters or weighting factors. Once the user has found a set of parameters they deem acceptable (or an updated composite image that meets predetermined requirements), the user may save the image.

Alternately, as part of the method of the system, the system may, based on extrapolation from pre-defined parameters, automatically compute weighting factors for the generation or the initial or any of the updated composite images. This automation may include retrieving a set of weighting factors from a previously-determined or pre-stored table of weighting factors. This may be stored in the processor or a database. Alternatively, it may be chosen mathematically to maximize or increase a given image parameter. For example, the contrast to noise ratio between two given regions of the image may be maximized or improved by intelligently selecting the weighting factors. This can be further expanded by dynamically altering the weighting factors at different parts of the image given the image data and known ideal penetration properties. Other image parameters may include, but are not limited to, image intensity, image noise, image spatial spectral power shape, relative region contrasts, or image histogram shape.

The method and system of the disclosure may find benefit in various applications. For example, the disclosure may be used in dynamic interventional medical imaging applications, where excess radiation exposure can be minimized or reduced if a first X-ray exposure, for example, at the highest kVp is performed on a region of interest. The user, or medical professional, can then apply the method of the disclosure to form an initial, and, if necessary, updated composite images at different kVp settings in order to review and discover the optimal, or a close to optimal, kVp or kVp setting required to visualize the region of interest before proceeding with the rest of the interventional procedure. This may save the medical professional and patient from excess, or extra, X-ray exposure in the traditional case to find the optimum energy for visualization.

In another application, in the examination of a multi-material object, the method of this disclosure may enable the simultaneous presentation of object images at multiple kVp to highlight different materials. As an example, it is well known that soft tissue imaging yields better contrast at lower kVp and bone imaging yields better contrast at high kVp. Many images may be generated from the same exposure(s) using different sets of weighting factors, allowing for a user to focus on different regions of interest in each one. Alternatively, images may be segmented and a composite image may be generated by selecting different weighting factors for different image segments. In another embodiment, the system may perform a measurement of a segment within the composite image and determine the weighting factor or factors based on the measurement.

In yet another application, in a radiotherapy or radiosurgery application, the method of this disclosure may enable the simultaneous high quality tracking of a tumor under treatment by using a high energy MeV beam and applying the method of the disclosure to reform the image at lower kVp settings typical for imaging, thereby saving the patient from additional radiation exposure.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

The invention claimed is:

1. A method of digital spectral adjustment for digital X-ray imaging comprising:
   obtaining at least two images generated by an X-ray imaging system, each of the at least two images including spectral information, the spectral information of each of the at least two images being distinct from each other;
   applying a weighting factor to the at least two images to generate weight factored images for each of the at least two images; and
   generating a composite image by combining the weight factored images of the at least two images wherein the composite image is spectrally distinct from the at least two images.

2. The method of claim 1 wherein the generating a composite image comprises:
   performing a linear combination of the weight factored images of the at least two images.

3. The method of claim 1 wherein the generating a composite image comprises:
   performing a non-linear combination on the weight factored images of the at least two images.

4. The method of claim 1 wherein the applying a weighting factor comprises:
   applying a same weighting factor to each of the at least two images.

5. The method of claim 1 wherein the applying a weighting factor comprises:
   applying a different weighting factor to each of the at least two images.

6. The method of claim 1 wherein the applying a weighting factor comprises:
   applying a predetermined weighting factor to each of the at least two images.

7. The method of claim 1 wherein the applying a weighting factor comprises:
   receiving an input from a user; and
   determining the weighting factor based on the input from the user.

8. The method of claim 1 further comprising, before applying a weighting factor:
   receiving the weighting factor from a user.

9. The method of claim 1 further comprising:
   calculating X-ray source settings based on characteristics of the composite image; and
   displaying the calculated X-ray source settings.

10. The method of claim 9 wherein the calculated X-ray source settings include a kVp setting or a filtration setting.

11. The method of claim 1 wherein the method is used in dynamic interventional medical imaging applications and the weighting factor is a value less than 1.

12. The method of claim 1 wherein the method is used in digital X-ray imaging of a multi-material object.

13. The method of claim 12 wherein the applying a weighting factor comprises:
   applying different weighting factors to each of the at least two images based on an area of interest of the multi-material object.

14. The method of claim 1 wherein the method is used in radiotherapy or radiosurgery.

15. The method of claim 14 wherein the generating a composite image comprises:
   generating a spectrally distinct composite image at lower kVp settings.

16. A computer-implemented method for spectral adjustment for digital X-ray imaging comprising:
   under the control of one or more computer systems configured with executable instructions,
   obtaining at least two images generated by an X-ray imaging system, each of the at least two images including spectral information, the spectral information of each of the at least two images being distinct from each other;
   applying a weighting factor to the at least two images to generate weight factored images for each of the at least two images; and
   generating a composite image by combining the weight factored images of the at least two images wherein the composite image is spectrally distinct from the at least two images.

17. The computer-implemented method of claim 16 wherein the generating a composite image comprises:
   performing a linear combination of the weight factored images of the at least two images.

18. The computer-implemented method of claim 16 wherein the generating a composite image comprises:

performing a non-linear combination on the weight factored images of the at least two images.

19. An X-ray imaging system comprising:
an X-ray source;
a multi-layer X-ray detector for generating a set of at least two initial images; and
a processor for weight factoring the at least two initial images to generate a weight factored image for each of the set of at least two initial images and for combining the weight factored images to generate a composite image, wherein the composite image is spectrally distinct from each of the at least two initial images.

20. The X-ray imaging system of claim 19 wherein the processor is integrated within the multi-layer X-ray detector.

* * * * *